United States Patent [19]

Valle

[11] 4,260,600

[45] Apr. 7, 1981

[54] METHOD OF TREATING DEPRESSION

[76] Inventor: Ronald Valle, 36 Fitch St., Carteret, N.J. 07008

[21] Appl. No.: 87,470

[22] Filed: Oct. 22, 1979

[51] Int. Cl.³ ................ A61K 31/135; A61K 31/165; A61K 33/02

[52] U.S. Cl. .................................... 424/166; 424/324; 424/330

[58] Field of Search ........................ 424/330, 324, 166

Primary Examiner—Stanley J. Friedman

[57] ABSTRACT

A method of treating depression by administering several active compounds throughout the day to a patient in need of such treatment. Also included are pharmaceutical composition claims incorporating these compounds.

3 Claims, No Drawings

METHOD OF TREATING DEPRESSION

BACKGROUND OF INVENTION

This invention relates to a method of treating depression by administering to a patient in need thereof several active compounds forming a novel combination. The invention also relates to pharmaceutical composition claims which incorporate the novel combination of active compounds. The compounds which form this novel combination are all known and are known for their adrenergic, antihistamine, analgesic or antipyretic uses, such as for example to relieve the symptons of a common cold.

I have found that by using a particular combination of these compounds, in a particular dosage range an antidepressive yet tranquilizing effect results. As such using my combination for this use avoids the use of other well known, costly, prescription only tranquilizers or antidepression drugs with their resultant potentially dangerous and in many cases unknown side effects and habit forming tendencies. The compounds which make up my combination are readily available, are quite safe for their uses, and are not as costly as the prescription tranquilizers and antidepressants.

The compounds to be administered are as follows:
(1) Phenylephrine hydrochloride which is (R)-3-hydroxy-α-[(methylamino)methyl]benzenemethanol hydrochloride. This compound alone has a therapeutic use as an adrenergic.
(2) Phenylpropanolamine hydrochloride which is chemically known as α-(1-aminoethyl)benzenemethanol hydrochloride. This compound when administered alone or in its hydrochloride salt form is an adrenergic (vasoconstrictor) agent also.
(3) Phenyltoloxamine which is N,N-dimethyl-2-[2-(phenylmethyl)phenoxy]ethanamine. This compound when administered as the dihydrogen citrate salt is useful as an antihistamine.
(4) Acetaminophen which is N-(4-hydroxyphenyl)-acetamide. This compound when administered alone is useful as an analgesic or antipyretic.
(5) Ammonium Chloride. This compound when administered alone has a therapeutic use in the pharmaceutical field as a systemic acidifier.

All the above compounds and their listed therapeutic uses in the pharmaceutical field are known from the prior art, i.e., all are disclosed in the Merck Index, Ninth Edition.

I have found, however, that these compounds or combinations thereof when administered to a patient in dosage ranges listed below have an anti-depressive yet tranquilizing effect. They are useful in treating schizophrenia. This combination of drugs (compounds as described more fully below) when administered in the proportions listed below provide a patient with normal sleep and make the patient less temperamental. In effect, the combination of compounds of this invention brings a patient to a normal mental state, makes him or her physically and emotionally more stable and decreases nervousness and tremors.

The combination of compounds of this invention can be administered in capsule form or they may be compressed into tablets using conventional pharmaceutical excipients, binders and lubricants and with or without other adjuncts. In fact, several of the active ingredients listed above come in commercially available cold and cough tablets and several examples of typical tablets are described. The compounds are preferably administered orally in daily amounts as follows:

| Acetaminophen | 100-1000 mg/day |
|---|---|
| Phenylephrine hydrochloride | 1-10 mg/day |
| Phenylpropanolamine | 5-30 mg/day |
| Phenyltoloxamine dihydrogen citrate | 5-30 mg/day |
| Ammonium chloride | 50-1000 mg/day |

A daily specific dose of the following compounds administered to a patient suffering from depression is exemplified below:

| Acetaminophen | 520 mg/day |
|---|---|
| Phenylephrine hydrochloride | 5 mg/day |
| Phenylpropanolamine | 20 mg/day |
| Phenyltoloxamine dihydrogen citrate | 25 mg/day |
| Ammonium Chloride | 320-480 mg/day |

A typical commercially available cough tablet contains the following ingredients:

| Acetaminophen | 260 mg. |
|---|---|
| Phenylephrine HCl | 2.5 mg. |
| Phenylpropanolamine hydrochloride | 10 mg. |
| Phenyltoloxamine | 12.5 mg. |
| Vitamin C | 20 mg. | and a glyceryl guaiacolate base.

Typical contents of another commercially available cough tablet:

| Ammonium chloride | 80 mg. |
|---|---| and a citric acid in a sugar base.

In order to obtain the specific dosage listed above, a patient suffering from depression can take two tablets during a 24 hour period of the first listed commercially available cough tablet and 4-6 tablets every 24 hours of the second commercially available cough tablet.

The compounds described in this invention are advantageously administered at a dosage range as described or a somewhat higher or lower dosage as the conditions warrant. It will be realized by those skilled in the art that the dosage range for any particular patient or human will depend on the severity of the depression or condition being treated, the weight of the patient and any other condition which a physician or other person skilled in the art will take account of.

What is claimed is:

1. A method of treating depression which comprises administering to a patient in need of such treatment a pharmaceutically effective combination of the following compounds in the following daily dosages

| Acetaminophen | 100-1,000 mg/day |
|---|---|
| Phenylephrine hydrochloride | 1-10 mg/day |
| Phenylpropanolamine | 5-30 mg/day |
| Phenyltoloxamine dihydrogen citrate | 5-30 mg/day |
| Ammonium chloride | 50-1,000 mg/day |

2. A method of treating depression which comprises administering to a patient in need of such treatment a pharmaceutically effective combination of the following compounds in the following daily dosages

| | |
|---|---|
| Phenylephrine hydrochloride | 1–10 mg/day |
| Phenylpropanolamine | 5–30 mg/day |
| Phenyltoloxamine dihydrogen citrate | 5–30 mg/day |
| Ammonium chloride | 50–1,000 mg/day |

3. A method of treating depression which comprises administering to a patient in need of such treatment a pharmaceutically effective combination of the following compounds in the following daily dosages

| | |
|---|---|
| Phenylephrine hydrochloride | 1–10 mg/day |
| Phenylpropanolamine | 5–30 mg/day |
| Ammonium chloride | 50–1,000 mg/day |

* * * * *